(12) United States Patent
Smith et al.

(10) Patent No.: US 6,936,156 B2
(45) Date of Patent: Aug. 30, 2005

(54) AUTOMATED SELF-CALIBRATING WATER QUALITY MONITORING SENSOR HOUSING ASSEMBLY

(75) Inventors: Kirk P. Smith, Mason, NH (US); Gregory E. Granato, Upton, MA (US)

(73) Assignee: The United States of America as represented by the Secretary of the Department of the Interior, Washington, DC (US)

( * ) Notice: Subject to any disclaimer, the term of this patent is extended or adjusted under 35 U.S.C. 154(b) by 0 days.

(21) Appl. No.: 09/881,243

(22) Filed: Aug. 30, 2001

(65) Prior Publication Data

US 2003/0042149 A1 Mar. 6, 2003

(51) Int. Cl.[7] .................. G01N 27/27; G01N 27/416
(52) U.S. Cl. .................. 205/775; 205/789; 204/409; 204/416
(58) Field of Search .................. 205/778.5, 781.5, 205/789, 775; 204/409, 411, 412, 416, 418, 419, 401; 422/50, 62, 82.01, 82.03, 82.02

(56) References Cited

U.S. PATENT DOCUMENTS

| | | | | |
|---|---|---|---|---|
| 4,762,594 A | * | 8/1988 | Guruswamy | 205/792 |
| 5,230,785 A | * | 7/1993 | Yager | 204/405 |
| 5,330,634 A | * | 7/1994 | Wong et al. | 205/777.5 |
| 5,496,450 A | * | 3/1996 | Blumenthal et al. | 205/782 |
| 5,653,862 A | * | 8/1997 | Parris | 205/777.5 |
| 5,993,742 A | * | 11/1999 | Binz et al. | 422/81 |
| 6,290,908 B1 | * | 9/2001 | Fukunaga et al. | 422/68.1 |

FOREIGN PATENT DOCUMENTS

| | | | | |
|---|---|---|---|---|
| JP | 10-337556 A | * | 12/1998 | C02F/1/00 |
| JP | 2001033297 A | * | 2/2001 | G01F/23/28 |

OTHER PUBLICATIONS

JPO abstract of Komatsu et al. (JP 10337556 A).*
JPO abstract of Takagi et al. (JP 2001033297 A).*

* cited by examiner

*Primary Examiner*—Alex Noguerola

(57) ABSTRACT

An automated self-calibrating water quality monitoring sensor housing assembly includes a number of ion-selective electrodes combined in a single flow train to provide for the multi constituent analysis of a number of samples without direct intervention by a human operator. An operator can enter the laboratory, connect sample bottles to an intake manifold, activate the device, and download data once the analysis is complete. With the exception of periodic probe maintenance, the system is designed to be self-calibrating and self cleaning.

13 Claims, 4 Drawing Sheets

Simplified schematic of one implementation of the automated self-calibrating water-quality-monitoring sensor-housing assembly.

Example process flow-train diagram for one implementation of the Automatic self-calibrating water-quality-monitoring sensor housing assembly program.

Figure 2. Simplified schematic of one implementation of the automated self-calibrating water-quality-monitoring sensor-housing assembly.

Temperature response and drift with time in readings from a solid state chloride probe.

AUTOMATED SELF-CALIBRATING WATER QUALITY MONITORING SENSOR HOUSING ASSEMBLY

FIELD OF THE INVENTION

The present invention relates to monitoring water quality and, more particularly, to an automated system for and method of monitoring water quality at ground water sampling sites, surface water sampling sites, and field laboratories.

BACKGROUND OF THE INVENTION

The Federal Government spends millions of dollars each year to characterize, monitor, and clean up ground- and surface-water contamination. Scientists in federal, state, and local agencies tasked with monitoring water quality must sample water quality on a frequent basis. Laboratory analysis costs often preclude collection and analysis of the large number of samples which could be used to provide detailed information on local geochemical conditions. While these are not absolutely necessary for local studies, these large numbers of samples are needed for using the data on a regional or national scale.

The U.S. Geological Survey conducted a study of the suitability of local data for regional or national monitoring programs and found that limitations in the availability of concentration data for major ions limited the usefulness of many data sets (Norris, 1990). This and other studies invalidated many data sets for national use on the basis of having too few samples and too few constituents analyzed to characterize the system of interest.

In investigating water quality using automated surface- and ground-water monitoring systems, the major ion chemistry of the systems of interest must be known (Granato and Smith, 1999; Bricker, 1998). While it is possible to take thousands of automated field measurements and hundreds of automated samples each year, the effort required for chemical titration or colorimetric methods to analyze a large number of these samples is time consuming and therefore expensive. Traditional laboratory analysis conducted in a central laboratory is expensive, and requires the additional time and expense required to ship the samples to the laboratory.

Traditional manual methods include deploying a field technician to draw samples from a well. The samples are then tested on site in accordance with established protocols, or are transported to a laboratory for analysis. However, manual methods for determining ground water quality have proven to be inherently inefficient. It is expensive to deploy field technicians to a site to retrieve test samples, and costs associated therewith only tend to increase in proportion to the number of wells tested within a given sampling site.

Personnel shortages, inclement weather, and other factors limit the frequency with which water samples can be taken manually. Typically, water samples can be tested only once or twice a month in areas having a high concentration of sites. Consequently change in water quality that take place over short periods of time, such as from surges of effluent and other contaminating influences into the water table, will often go undetected.

Improvements in assessing water quality rely on automated methods using passive techniques. In this method, a data logger controls a probe in a well to make measurements from which water quality can be determined. Automated systems have, in other monitoring applications, outperformed their manual counterparts. The use of a data logger relieves field technicians of the job of having to capture the samples to be tested. Automated systems can also be programmed to take a greater frequency of measurements as compared with measurements taken by manual methods. Since data collected by automated systems are often electronically stored, they are easier to use.

It was originally hoped that automated, self-calibrating water quality monitoring sensors could be used in an on-line water quality analysis system at each field site of interest. However, field trials indicated that, with current technology, ion selective probes would not produce consistent or reliable measurements in the field because of variations in suspended sediment, system pressure, air, and water temperature. Microbial growth and other such factors could affect measured values even with a rigorous (weekly) maintenance program.

Manual use of ion-specific probes to measure water quality have been an accepted method of water quality analysis for a number of years; Evans, 1987; Fishman and Friedman, 1989. Process flow monitoring of public and/or private water supplies and wastewater utilities, process-flow monitoring in aquaculture, and analysis procedures used in water quality laboratories has been done. However, these applications are characterized by high volume continuous operations in industrial settings which are costly to purchase and maintain. Self-calibrating industrial sensors currently available are relatively expensive (on the order of about $1,000 to $10,000 per constituent), and are limited to one constituent per unit from a known sampling matrix at a specific temperature. Also, because industrial probes are designed for process control, they are often designed to take very small subsamples and process these samples off line.

Granato et al., in U.S. Pat. No. 6,021,664, the entire contents of which are hereby incorporated by reference, disclose an automated groundwater monitoring system and method. This apparatus is designed for use on site.

Pace, U.S. Pat. No. 4,225,410, discloses an integrated miniaturized array of chemical sensors comprising ion-sensitive electrodes for concurrently analyzing a number of analytes in a fluid sample. However, this device is disposable, so there is no need to purge the system.

Tomita, in U.S. Pat. No. 5,234,568, discloses an apparatus for simultaneous measurement of a plurality of ionic concentrations using ion selective electrodes formed on the same electrode sheet.

Kurland, in U.S. Pat. No. 4,216,671, discloses a method for automatically cleaning sensing probes of water quality monitoring apparatus.

Cormier et al., in U.S. Pat. No. 5,019,238, disclose means for quantitative determination of analytes in liquids comprising units arranged seriatim to provide narrow through passageways linked to each other for determination by electrodes. Auxiliary passageways are used to allow flushing of a first sample chamber without contamination from a second sample chamber, as well as to allow measurement of a calibrating fluid.

Moss et al., in U.S. Pat. No. 5,483,164, disclose a water quality sensor apparatus for sensing a plurality of different characteristics relating to water quality. The sensors are all supported on a ceramic substrate, and signals from the sensors are fed to signal conditioning circuits which are connected to processor display and data logging units.

Brindak, in U.S. Pat. No. Re 33,468, discloses an apparatus for testing fluids for fouling which is connected in fluid flow communication to a heat transfer apparatus for in-situ testing and generation of foulant data to permit substantially simultaneous implementation of antifoulant protocol. A heating member is provided for controlled heat input, and data are simultaneously monitored and recorded.

Barcelona et al., in U.S. Pat. No. 4,803,869, disclose a portable apparatus for flow-through measurement of ground water comprising four or more electrode sensors. Electrode and other sensor malfunctions can readily be noted by calibration procedures. Gas or foreign matter is removed by dismantling, cleaning, and reassembly.

Millo, in U.S. Pat. No. 5,879,692, discloses an effluent monitoring system in which a plurality of threshold values are programmed and provides a variable and dynamic response to effluent property detecting probes for controlling a sampler device, alarm, or the like.

SUMMARY OF THE INVENTION

It is an object of the present invention to overcome the aforesaid deficiencies in the prior art.

It is another object of the present invention to provide an automated self-calibrating water quality monitoring sensor housing assembly.

It is a further object of the present invention to provide a water quality monitoring sensor housing assembly which can analyze a number of samples without direct intervention by a human operator.

According to the present invention, an automated self-calibrating water quality monitoring sensor housing assembly includes a number of ion-selective electrodes and probes combined in a single flow train to provide for the multi constituent analysis of a number of samples without direct intervention by a human operator. An operator can enter the laboratory, connect sample bottles to an intake manifold, activate the device, and download data once the analysis is complete. With the exception of periodic probe maintenance, the system is designed to be self-calibrating and self cleaning.

The automated self-calibrating water quality monitoring sensor housing assembly includes a flow train with ports for introducing a number of ion-selective electrodes and probes to measure other properties and constituents such as temperature, pH, and conductance (as a measure of total ionic strength). The flow train can be configured for a single pass or for repeated measurements in a recirculation loop. The housing assembly includes inlet ports for introducing purified fluids such as nitrogen to purge the system; deionized water to clean the system between samples to apply dilutions to samples collected, and/or to provide a quality assurance/quality control measure for the quality of deionized water produced on site; and ports for introducing standard reference solutions to calibrate water quality probes, to provide ionic strength adjustments, and/or to spike environmental samples with known volumes of standard solutions.

DETAILED DESCRIPTION OF THE INVENTION

The automated self-calibrating water quality monitoring sensor housing assembly of the present invention is designed to facilitate analysis of one or more samples for a number of major consistuents. Upon activation, the device and process perform the following steps:

1. Rinse the system with fluids such as deionized water and gas-purge the system;

2. Activate the system and perform diagnostic checks;

3. Introduce a series of standard reference solutions for each water quality monitoring probe and rinse the system between calibrations as appropriate;

4. Calculate the slope and intercept of each probe using data from appropriate standard solutions;

5. Notify the operator using data from a control panel indicator and/or a message transmitted by the computer controller using a voice modem and/or appropriate electronic mail software if the operational parameters of the probes do not meed prespecified criteria.

Probe readings can be easily displayed using an external analog or digital display which is either proximate to the unit or in a remote area. Alternatively, probe readings and system status may also be displayed and downloaded on a computer terminal that is interfaced with the electronic terminal. Using logic based programming and appropriate software, all of which are known to those skilled in the art, the computer can analyze data downloaded from the electronic control module and then execute specific preprogramed tasks in response thereto. Among these tasks can be e-mail messages to remotely located operators advising them of the water quality conditions. Predetermined voice messages or page numbers programmed into the controller can be transmitted by a voice/data modem in response to prespecified criteria. For example, if the level of a specific constituent exceeds regulatory thresholds established by a total maximum daily threshold, the electronic controller can notify the appropriate persons.

6. Continue to analyze water quality in one or more water samples if the probes are working within established specification;

7. Provide the option of injecting a pH buffer or ionic strength adjuster if the volume of standard reference solution, deionized water, or a reference solution prepared by the operator to obtain quality assurance/quality control spike or dilution measurements;

9. Wash and purge the system between samples as appropriate;

10. Optionally recalibrate after a number of samples are measured to detect drift of probe calibration parameters, the data for each sample, and any other pertinent measures for each activation period; and 11. Produce and transmit a computer file to record the results of the sampling round.

Figure 1:
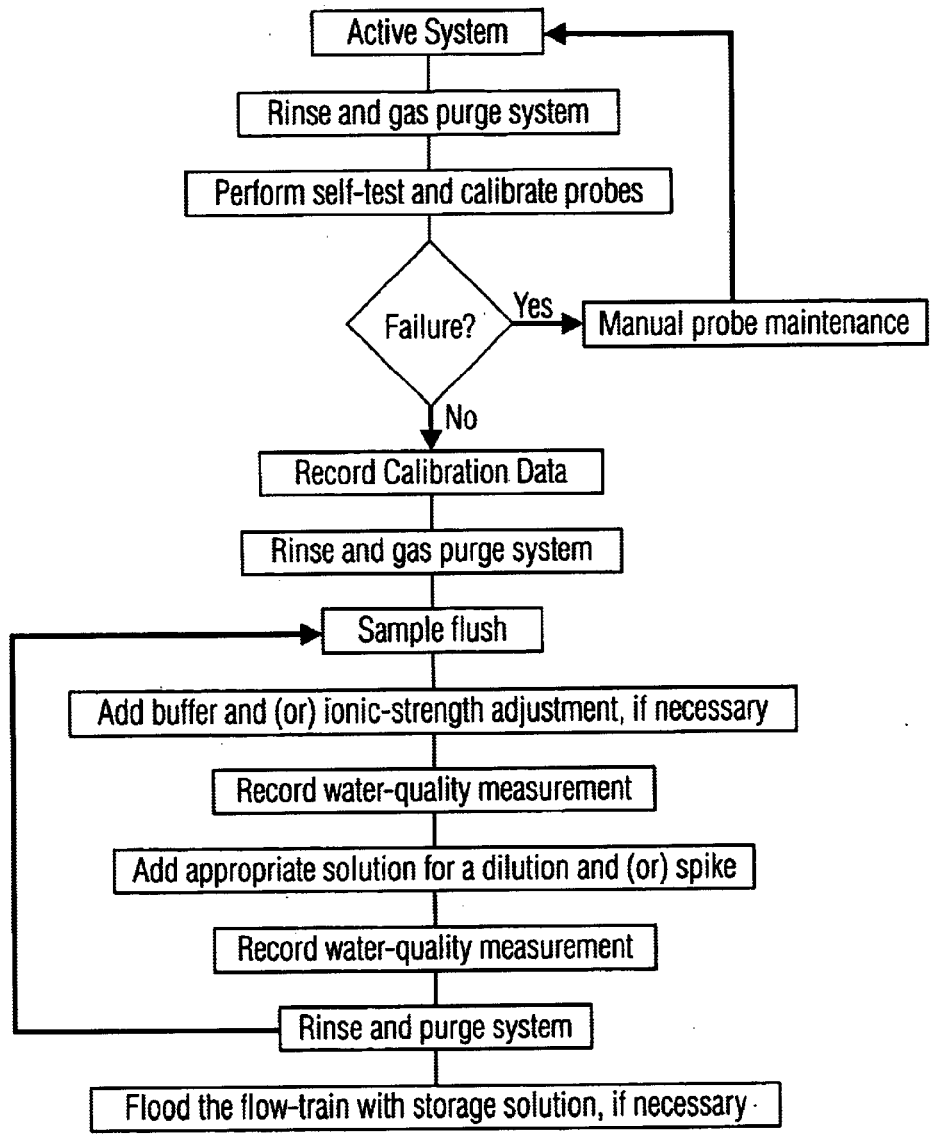
FIG. 1 is a process flow diagram for one embodiment of the automated self-calibrated water quality monitoring sensor housing assembly of the present invention.

A flow chart of this process is shown in FIG. 1. Once the system is activated, the system is rinsed and gas purged with nitrogen. The system then performs a self test and calibrates the probes. Self-testing attributes can be incorporated throughout the measurement and calibration cycle. For example, the presence of fluid in the flow train, as measured by an integral flow meter can result from a pump malfunction or a break in the line. In either case, the measurement or calibration cycle can be halted and the error recorded. These data are then transmitted, or a pager or voice message sent by the voice/data modem. A conventional computer program can be used to document how the system as built and tested works. If a failure is detected, there is a provision for manually maintaining the probes. Otherwise, the calibration data are recorded. The system is once again rinsed and gas purged (e.g., with nitrogen), and a sample is introduced into the system. Optionally, buffer and/or ionic-strength adjustment is added, and the measurement of water quality is recorded. Appropriate solution for a dilution and/or spike is added, and again the water quality measurement is recorded. The system is then rinsed and gas purged, ready for introduction of another sample. Once all samples have been analyzed, the flow train is flooded with storage solution if necessary.

With respect to self-testing and calibration, the instructions depend upon the complexity of the system and specific probes used. For example, calibration using an incremental titration method would use only one standard solution. However, where several standards are used, such as ionic strength or pH adjustment of sample water, different software and/or hardware procedures are required. These can readily be chosen by one skilled in the art without undue experimentation.

The status of the system may be monitored based upon instrument and equipment signals indicating, for example, the existence of an error condition. These conditions may include low sample level, insufficient power supply, malfunctioning probes, and an indication that at least one water quality attribute obtained during the measuring step lies outside a predetermined range. Once an error condition has been detected, the process is terminated and a warning signal is automatically transmitted to the operator.

The device of the present invention is not designed to replace conventional laboratory sampling, but rather would supplement traditional methods within an established quality-assurance/quality control program to better characterize the system under scrutiny in comparison with traditional laboratory and field analysis methods.

Figure 2:
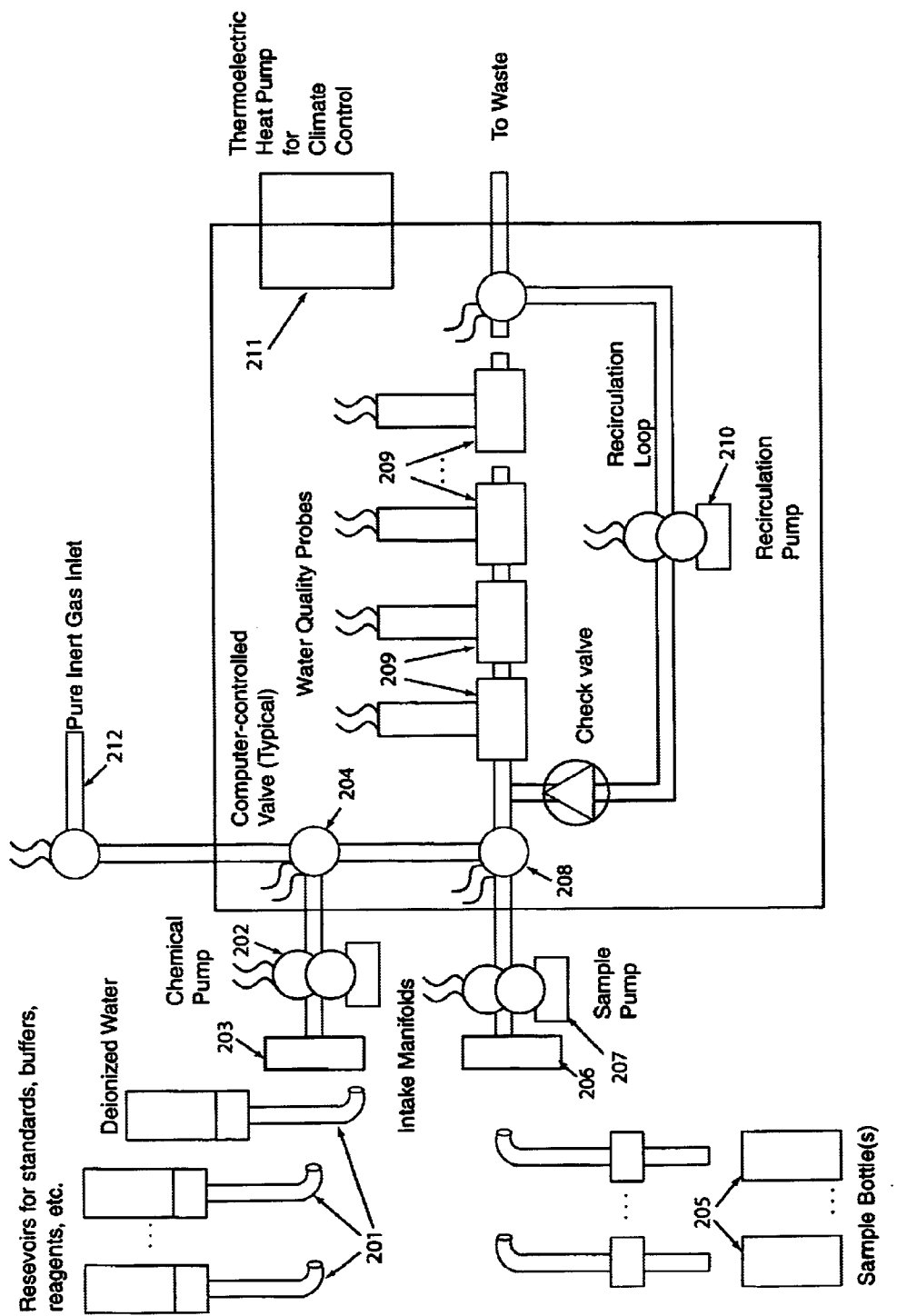
FIG. 2 is a schematic of one embodiment of the automated self-calibrated water quality monitoring sensor housing assembly of the present invention.
Figure 3:
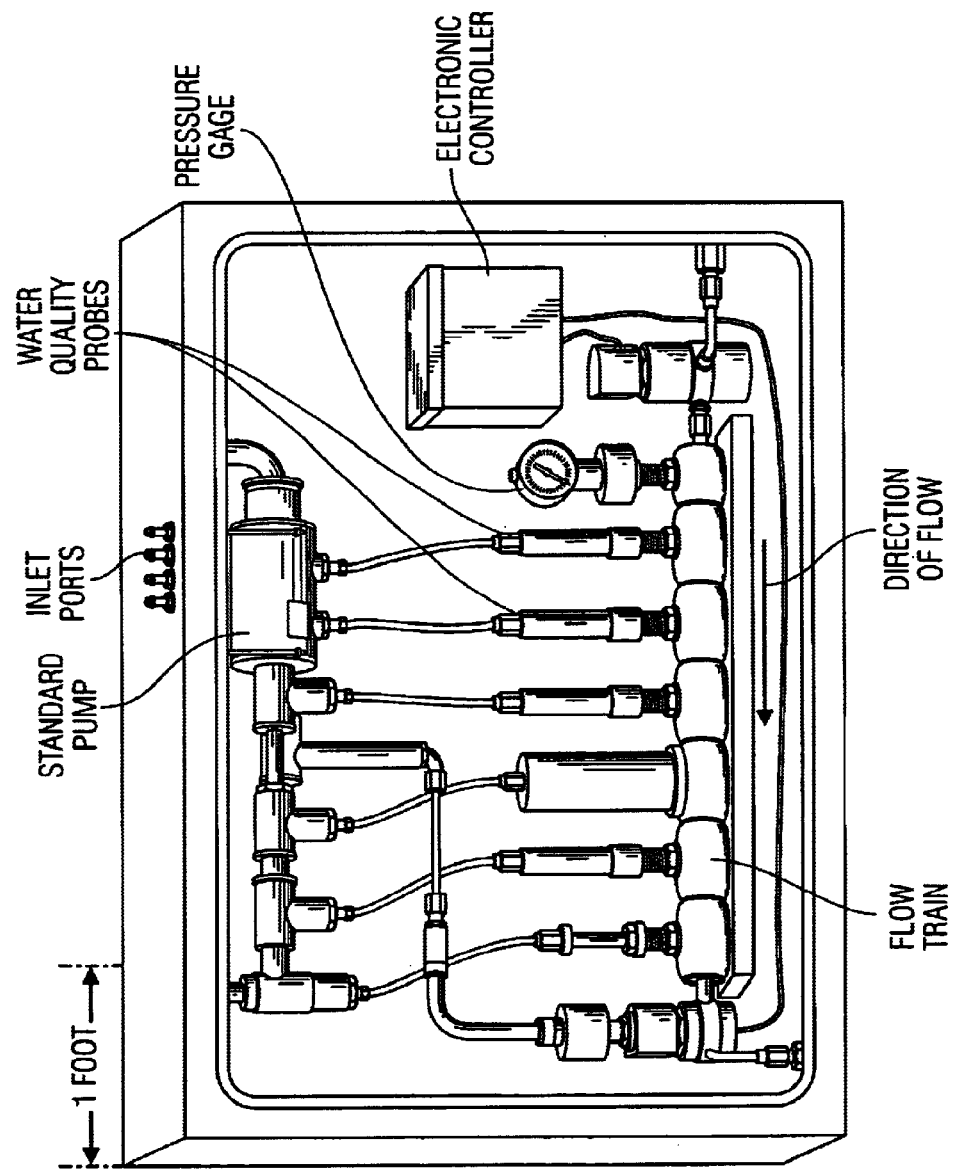
FIG. 3 is an annotated photograph of a prototype of an automated self-calibrated water quality monitoring sensor housing assembly of the present invention.

The automated self-calibrating water quality monitoring sensor housing assembly 200 can be designed to handle one or more samples at a time, depending upon the input structure, as shown in FIG. 2. Reservoirs 201 are provided for standards, buffers, reagents, and the like, as well as for deionized water. A pump 202 causes these fluids to flow through intake manifold 203 into a conventional computer-controlled valve 204. Sample bottles 205 are connected through an intake manifold 206 to a sample pump 207, then through a conventional computer-controlled valve 208. Both the sample and the standards, buffer, reagents, etc., as appropriate, are sent to water quality probes 209. After analysis, the solutions are flowed out of the device to appropriate disposal of the waste. A recirculation pump 210 is provided to recirculate the samples and reagents, etc. as necessary. An optional thermoelectric heat pump 211 is provided for temperature control of the analysis. An inlet 212 for pure inert gas, such as nitrogen, is provided so that the entire system can be flushed with inert gas. The electronic control module is not shown in the figures, because this can be arbitrarily chosen, determining upon the type of data collection/retrieval desired. This electronic control module, for example, can be a data logger, a personal computer, or a remote server.

The system can include probes for a plurality of water quality control measurements, with one probe provided for each measurement desired. Among the conditions measured are temperature, specific conductance, dissolved oxygen content, pH, ammonium ion, chloride ion, etc.

The device can be either a bench top or a mobile unit for use in locations which have the proper power, system pressure, climate control, and electrical shielding for reliable and consistent measurement. The device can be used with either a commercial data logger or a personal computer with the correct interface hardware. The probes for use in this device are conventional water quality measurement probes that can be installed in a flow train of reasonable dimensions for sample analysis. Examples of these probes include nitrate- or chloride-selective ion selective electrodes. However, the present invention is in no way limited to the types of probes used. Typical sample volumes are less than 0.5 liter. The unit can be designed as a simple, low cost installation with a few features, or may include a plurality of features to provide extensive analysis of water quality. Any features which can be automatically determined can be used for monitoring water quality.

The most important water quality parameters include pH, specific conductance, dissolved oxygen and turbidity. Depending upon the quality of the water being measured and the desired time frame for manual maintenance necessary, any or all of these parameters can be incorporated in a device for standard water quality measurement. More sophisticated monitoring may include measuring dissolved major ions such as sodium, calcium, and chloride; dissolved metals such as lead, cadmium, and copper; and dissolved nutrients, such as ammonium, nitrate, and nitrite, as measured by ion specific probes. Additionally, many other probes and sensors are currently available for organic and inorganic constituents, and these can be incorporated in the system of the present invention. Thermoelectric heat pump technology or any conventional temperature control (thermal management) means can be used to maintain standard temperature.

The automated self-calibrating water quality monitoring sensor housing assembly of the present invention is particularly advantageous in that it automatically conditions the system, cleans the flow train, calibrates the pumps, and makes one or more measurements on one or more samples as desired. The process of the present invention has the advantage of allowing precise automated injection of one or more ionic strength adjustors, pH buffers, deionized water, and/or standard solutions. The process then provides for measuring the effects of the additions so as better to interpret the results of probe measurements in solution. The process and apparatus are designed to process a representative sample volume. The device is also designed to provide relatively low cost analysis because it can accept a series of commercially available water-quality probes that will fit within the dimensions of the flow train. Provisions for self-calibration and the ability to maintain standard temperatures will reduce variance in system measurements in field laboratories that do not have precise temperature control.

Figure 4:
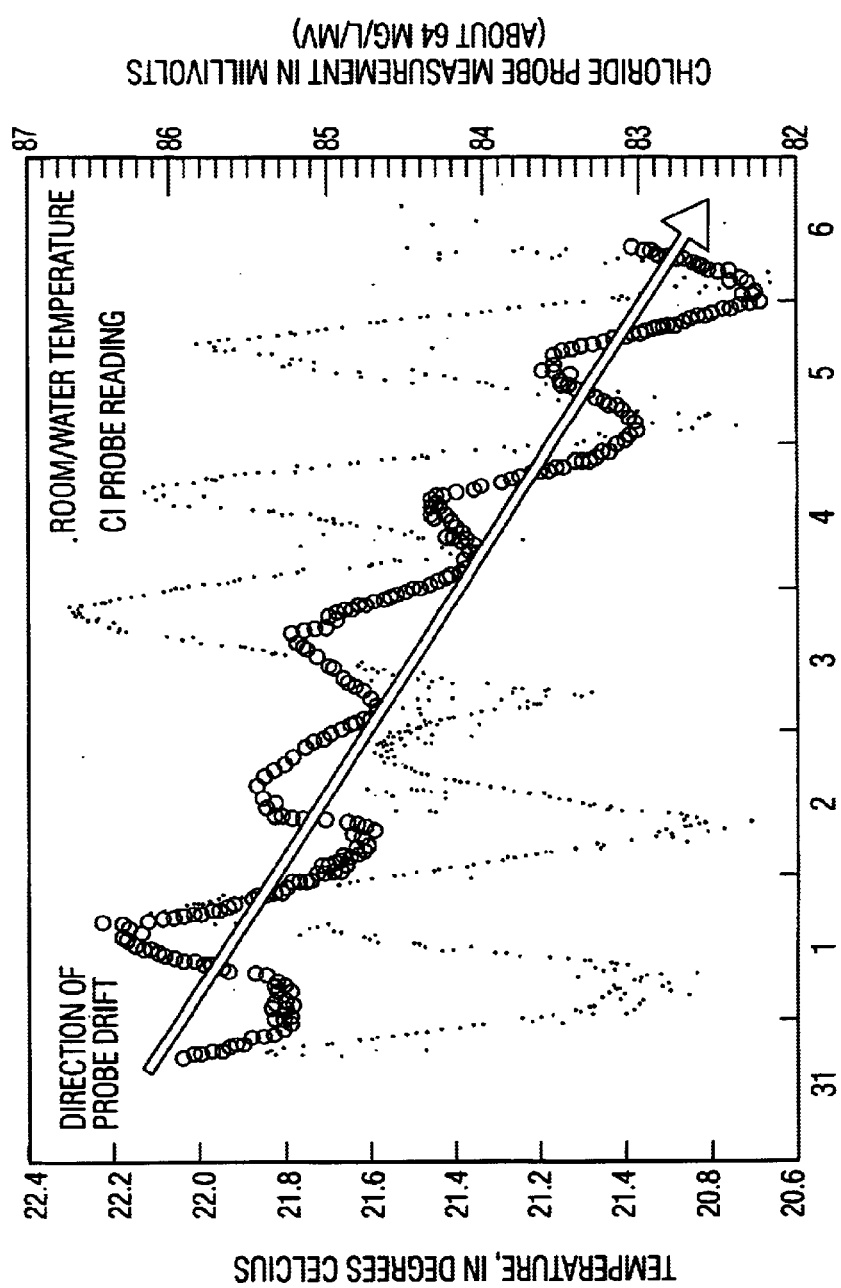
FIG. 4 is a graph showing temperature response and drift with time in readings from a solid state chloride probe.

FIG. 4 illustrates the variations in measurement of chloride ion with variations in temperatures. To obtain the values shown in FIG. 4, continuous values were obtained from an ISI solid-state ion selective chloride probe and a general-purpose type E thermocouple temperature probe connected to a Campbell Scientific Inc. CR10 data logger. The probes were inserted into a sealed laboratory jar containing a chloride standard of approximately 64 mg/L for a period of one week.

The system of the present invention is useful because of the ability to automatically rinse and gas purge the system between sequential samples, and to perform self calibration on more than one water-quality probe in the same flow train. The system includes a computer control needed to halt the measurement process and contact an operator to service the water quality probes. The system is capable of metering one or more chemical solutions in the flow train during a measurement cycle in order to elicit a measurement response. A low power thermoelectric heat pump or other conventional source of heat or cooling is used to maintain standard temperatures, thus obviating errors due to temperature changes.

The foregoing description of the specific embodiments will so fully reveal the general nature of the invention that others can, by applying current knowledge, readily modify and/or adapt for various applications such specific embodiments without undue experimentation and without departing from the generic concept. Therefore, such adaptations and modifications should and are intended to be comprehended within the meaning and range of equivalents of the disclosed embodiments. It is to be understood that the phraseology or terminology employed herein is for the purpose of description and not of limitation. The means and materials for carrying our various disclosed functions may take a variety of alternative forms without departing from the invention. Thus, the expressions "means to . . . " and "means for . . . " as may be found in the specification above and/or in the claims below, followed by a functional statement, are intended to define and cover whatever structural, physical, chemical, or electrical element or structures which may now or in the future exist for carrying out the recited function, whether or not precisely equivalent to the embodiment or embodiments disclosed in the specification above; and it is intended that such expressions be given their broadest interpretation.

What is claimed is:

1. An automated process for monitoring water quality comprising:

providing a system for monitoring water quality, the system comprising a plurality of ion-selective electrodes and probes combined in a single flow train for multi-constituent analysis of a plurality of samples and a recirculation pump for optionally recirculating samples and reagents;

rinsing and gas purging the system for monitoring water quality;

self-testing and calibrating the probes;

recording calibration data;

rinsing and gas purging the system;

optionally notifying an operator of the system if the operational parameters of the probes do not meet prespecified criteria;

introducing sample to be tested into the system;

optionally adding buffer or ionic-strength adjusting solution to the probes;

monitoring water quality by measuring the analytes in the sample with the probes;

recording the measurements;

optionally conducting a second measuring step adding appropriate solution to dilute the sample in the probes or create a spike, measuring the analytes to be determined in the sample, and recording the water-quality measurement;

optionally recalibrating the system after a number of samples are measured to detect drift of probe calibration parameters; and producing or transmitting a computer file to record the results of the monitoring process.

2. The process according to claim 1 wherein once the water quality conditions are monitored, further notifying an operator of the results obtained for the water quality conditions monitored.

3. The process according to claim 2 wherein the operator is notified using a voice modem or electronic mail.

4. The process according to claim 1 wherein the status of the system is monitored based upon signals indicating the existence of at a a least one error condition.

5. The process according to claim 4 wherein the error conditions are selected form the group consisting of low sample level, insufficient power supply, malfunctioning probes, and at a a least one measurement lying outside a predetermined range.

6. The process according to claim 4 wherein, once an error condition is detected, the process is terminated and a warning signal is automatically transmitted to an operator.

7. The process according to claim 1 wherein the probes are configured in a single flow train.

8. An automated self-calibrating water quality monitoring system housing assembly comprising:

a plurality of ion-selective electrodes and probes combined in a single flow train for multi-constituent analysis of a plurality of samples;

inlet ports for introducing purified gases into the system to gas purge the system and to clean the system between samples;

reservoirs for solutions used in water quality monitoring;

a pump for introducing said solutions from the pulsating pressure of the order of 50 to 450 mbar to the reservoirs through ports to the sample containers;

sample containers connected to a sample pump for the sample to be sent through the flow train for analysis;

a recirculation pump for optionally recirculating samples and reagents; and an electronic control module for controlling the system and collecting data obtained from the electrodes and the probes.

9. The system according to claim 8, further including a heat pump for temperature control.

10. The system according to claim 8 wherein the probes are selected from the group consisting of temperature, conductance, dissolved oxygen content, turbidity, and pH.

11. The system according to claim 8, wherein the ion-selective electrodes are selective for ions selected from the group consisting of ammonium, chloride, sodium, calcium, lead, cadmium, copper, nitrate, and nitrite.

12. The system according to claim 8 wherein the flow train is configured for repeated measurement in a recirculation loop.

13. The system according to claim 8 wherein the solutions are selected from the group consisting of deionized water, ionic strength adjustment solutions, and known volumes of standard solutions.

* * * * *